(12) United States Patent
Evans et al.

(10) Patent No.: US 9,028,771 B2
(45) Date of Patent: May 12, 2015

(54) SATURATION ASSAY

(75) Inventors: Douglas Robert Evans, Chester (GB);
Gerald John Allen, Caythorpe (GB);
Carolyn Jennifer Ruddell, Wirral (GB)

(73) Assignee: Platform Diagnostics Limited, Ossett, West Yorkshire (GB)

( * ) Notice: Subject to any disclaimer, the term of this patent is extended or adjusted under 35 U.S.C. 154(b) by 840 days.

(21) Appl. No.: 12/514,397

(22) PCT Filed: Nov. 9, 2007

(86) PCT No.: PCT/GB2007/004290
§ 371 (c)(1),
(2), (4) Date: May 11, 2009

(87) PCT Pub. No.: WO2008/056165
PCT Pub. Date: May 15, 2008

(65) Prior Publication Data
US 2010/0062544 A1    Mar. 11, 2010

(30) Foreign Application Priority Data
Nov. 10, 2006 (GB) .................................. 0622404.2

(51) Int. Cl.
*G01N 33/558* (2006.01)
*G01N 33/538* (2006.01)
(Continued)

(52) U.S. Cl.
CPC ........ *G01N 33/538* (2013.01); *G01N 33/54366* (2013.01); *G01N 33/54313* (2013.01);
(Continued)

(58) Field of Classification Search
CPC .......... G01N 33/538; G01N 33/54313; G01N 33/54366; G01N 21/8483; G01N 1/40; G01N 1/4005; G01N 1/4077; G01N 30/90; G01N 33/536; G01N 33/537; G01N 33/54306; G01N 33/58; G01N 33/585; B01L 2300/0825; B01L 2300/0816; B01L 2300/0887; B01L 2200/0647; B01L 2200/0652; B01L 2200/0668
USPC ........... 435/7.9, 7.91, 7.92, 7.93, 960, 973, 4, 435/6.1, 6.11, 6.19, 7.1–7.95
See application file for complete search history.

(56) References Cited

U.S. PATENT DOCUMENTS 4,459,361 A  *  7/1984  Gefter .......................... 436/523
4,552,839 A     11/1985  Gould et al.
(Continued)

FOREIGN PATENT DOCUMENTS

EP    0254117 A2    1/1988
EP    0293779 A1    12/1988
(Continued)

OTHER PUBLICATIONS

Brown, B. L. et al., "A Simple and Sensitive Saturation Assay Method for the Measurement of Adenosine 3' : 5'-Cyclic Monophosphate," Biochem. J., vol. 121, pp. 561-562 (1971).
(Continued)

*Primary Examiner* — Melanie Y Brown
*Assistant Examiner* — Erik B Crawford
(74) *Attorney, Agent, or Firm* — Janet Sleath; Speckman Law Group PLLC

(57) ABSTRACT

The invention provides a modified form of saturation assay, which is based on the measurement of a free or unbound labelled reagent fraction (such that there is an increase in signal in the presence of analyte) and employs trapping zones to concentrate said unbound or free labelled fraction to avoid loss of sensitivity. Preferably, the assay is a membrane assay.

9 Claims, 2 Drawing Sheets

(51) Int. Cl.
  *G01N 33/543* (2006.01)
  *G01N 33/53* (2006.01)
  *B01L 3/00* (2006.01)
  *B01D 15/34* (2006.01)

(52) U.S. Cl.
  CPC ..... *G01N33/5302* (2013.01); *B01L 2300/0825* (2013.01); *B01L 2300/0681* (2013.01); *B01L 2300/0816* (2013.01); *B01L 3/5023* (2013.01); *B01L 3/502753* (2013.01); *B01L 3/502761* (2013.01); *B01L 2200/0647* (2013.01); *B01L 2200/0668* (2013.01); *B01D 15/34* (2013.01); *G01N 33/558* (2013.01); *Y10S 435/97* (2013.01); *Y10S 435/971* (2013.01)

(56) References Cited

U.S. PATENT DOCUMENTS

| | | | |
|---|---|---|---|
| 5,231,035 | A | 7/1993 | Akers, Jr. |
| 5,451,504 | A * | 9/1995 | Fitzpatrick et al. ............ 435/7.2 |
| 5,500,375 | A * | 3/1996 | Lee-Own et al. ............ 436/514 |
| 5,565,366 | A | 10/1996 | Akers, Jr. |
| 5,827,749 | A | 10/1998 | Akers, Jr. |
| 6,087,185 | A * | 7/2000 | Lee-Own et al. ............ 436/514 |
| 6,121,008 | A * | 9/2000 | Fitzpatrick et al. ............ 435/7.9 |
| 6,235,241 | B1 | 5/2001 | Catt et al. |
| 2002/0187071 | A1 | 12/2002 | Law |
| 2004/0241879 | A1 * | 12/2004 | Robinson ..................... 436/514 |
| 2004/0248222 | A1 | 12/2004 | Root et al. |

FOREIGN PATENT DOCUMENTS

| | | |
|---|---|---|
| EP | 0297292 A2 | 1/1989 |
| EP | 0940681 A2 | 9/1999 |
| GB | 2045431 A1 | 10/1980 |
| JP | 2001-033453 A | 2/2001 |
| WO | 9205440 A1 | 4/1992 |
| WO | 0020866 A1 | 4/2000 |
| WO | 0131337 A2 | 5/2001 |

OTHER PUBLICATIONS

Kutter, Dolphe, et al., "Screening for Oligoalbuminuria by Means of Micral-Test II a New Immunological Test Strip," Eur J Clin Chem Clin Biochem, vol. 33, No. 4, pp. 243-245 (1995).

Wilson, Robert, et al., "Electrochemiluminescence enzyme immunoassay for TNT," The Analyst, vol. 128, pp. 480-485, (2003).

Eiken Chem Co Ltd, "Measuring Method for Ligand," JP Patent No. JP2001-033453A, Published Feb. 9, 2001, Excerpts, paragraphs [0010], [0013], [0017], and [0052]-[0057], JPO Office Action dated Mar. 2, 2012.

* cited by examiner

Figure 1. Assembly of test strips with a primary agglutinate trapping membrane.
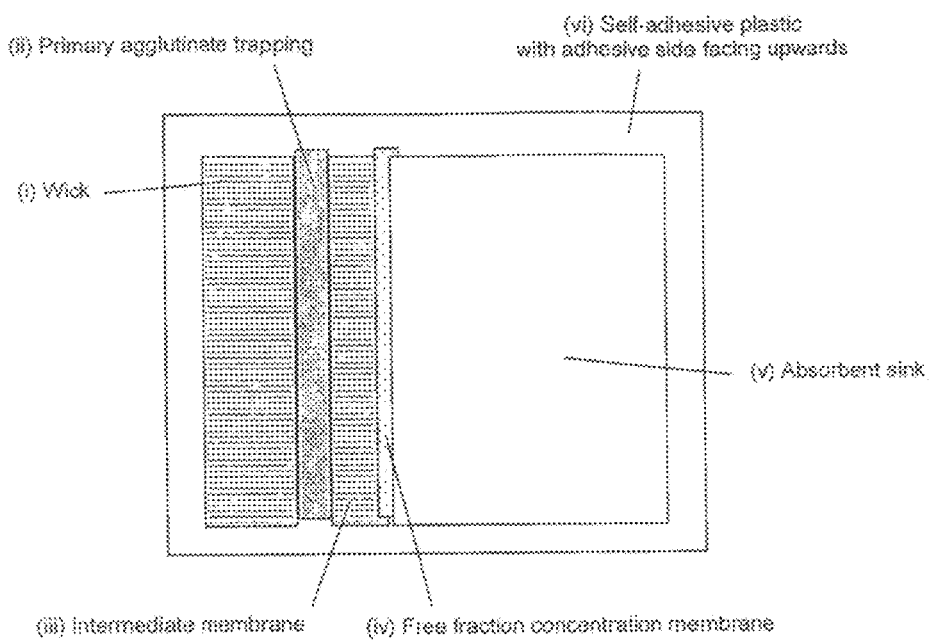
Figure 2. Assembly of test strips with a chromatographic agglutinate separation membrane.
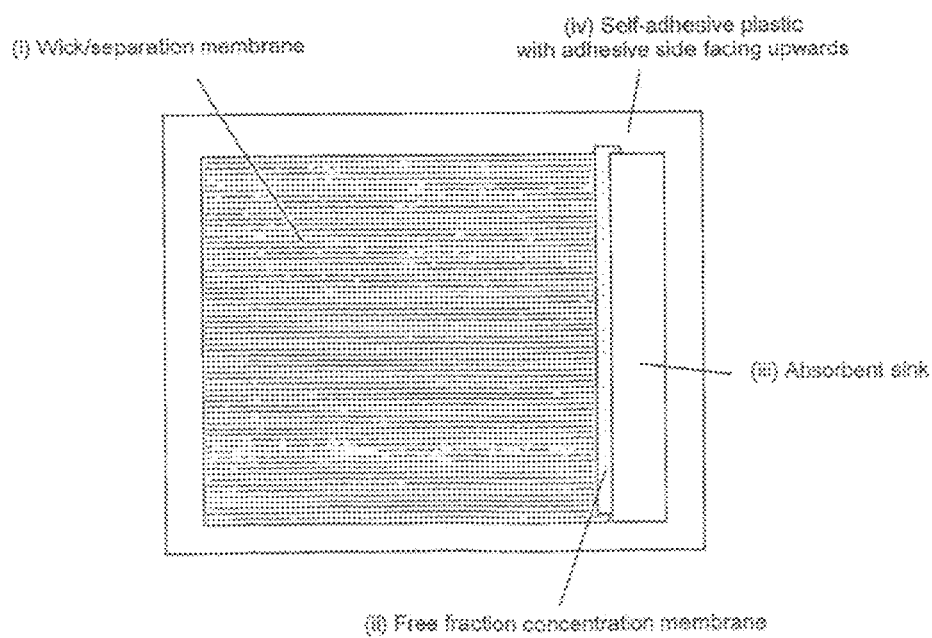

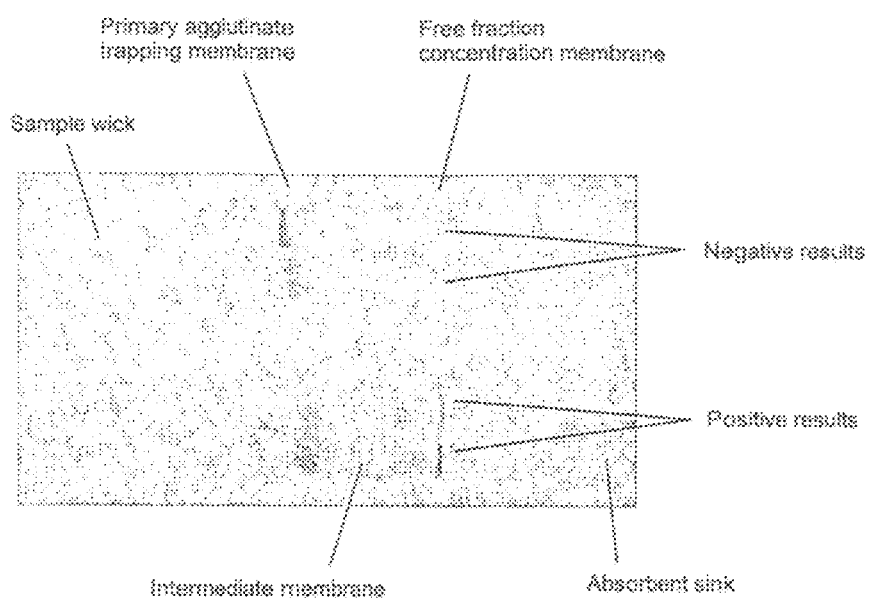
Figure 3. Photograph of positive vs negative test results

SATURATION ASSAY

REFERENCE TO RELATED APPLICATIONS

This application is the U.S. national phase entry of International Patent Application No. PCT/GB2007/004290, filed Nov. 9, 2007, which claims priority to UK Patent Application No. 0622404.2, filed Nov. 10, 2006.

FIELD OF INVENTION

The present invention relates to an improved assay for detection of analytes in a sample. In particular, the invention relates to assay devices, kits comprising means for conducting such an assay, and an assay method for the detection of analyte in a sample based on binding competition, generally between analyte and analyte analogue for binding sites on an analyte-binding reagent.

BACKGROUND

Binding assays are a well-established technique for detecting and quantifying analytes in samples. They are particularly useful for detecting and/or measuring substances in biological samples as an aid to disease diagnosis and prognosis, and for predicting a patient's response to therapy. Often they take the form of immunoassays in various formats in which the analyte-binding reagent is an antibody or functional fragment thereof.

The majority of such assays are based on the 2-site or "sandwich" format, which is very useful for analytes that can bind to 2 or more antibodies or receptors simultaneously, but are unsuitable for haptens (which, because of their size, can often only bind to one antibody at a time). For hapten assays, it is usually necessary to utilise saturation-type assays which are typically used for antigen-antibody assays. These are assays whereby sample analyte competes with a fixed quantity of reagent analyte (or analyte analogue, which has been chemically modified such that it is, for example, detectable or immobilised) for a limited number of binding sites on an analyte-binding reagent (e.g. antibody). In saturation assays, the total number of analyte and analyte-analogue molecules is greater than the total number of binding sites on the analyte binding reagent.

These assays can be direct competition format (where sample analyte, analogue and analyte-binding reagent react simultaneously) or indirect competition format (whereby the sample analyte and analyte-binding reagent are allowed to interact together first, and then reacted with the analyte analogue). This latter format is also known as a sequential or back-titre assay. Competition assays generally utilize an analyte analogue labelled with a detectable signal moiety and an unlabelled antibody (frequently attached to a solid phase). The closely-related 1-site immunometric format generally utilizes an antibody labelled with a detectable moiety and an analyte analogue immobilized onto a solid-phase.

The amount of analyte analogue that becomes bound to the analyte binding reagent will thus be inversely proportional to the amount of analyte in sample and by detecting the amount of bound analyte analogue (for competition assays) or bound analyte binding reagent (for 1-site immunometric assays) the presence and/or amount of analyte in a sample can be determined. Detection of a decrease in signal is more difficult than an increase in signal from a negative background, and frequently results in a loss of sensitivity, especially if detection is visual. Measurement of the free or unbound signal overcomes this, but usually the free fraction is present in a larger volume and is diffuse, again resulting in a loss of sensitivity.

There is a growing need for assays to be performed closer to the patient, primarily to shorten the time taken to provide results. Such assays are known as Point-of-Care assays, and typically need to be robust and simple to perform since they are carried out in a non-laboratory setting, frequently by non-skilled staff. Ideally, they should be fully self-contained and require no ancillary equipment (with the possible exception of a reader). Point-of-Care assays need similar sensitivity to laboratory-based assays if they are to have any clinical use. However, conventional immunoassays often comprise complex protocols and detection systems, meaning that they are often unsuitable for point-of-care type use.

Specific Point-of-Care assays have been developed. The most common are lateral flow assays. Often, these are based on a labelled mobile component (e.g. coloured particle-labelled antibody), an immobilised component (e.g. antibody stripe or dot) and a membrane through which sample is caused to move by capillary action. In the presence of analyte, a "sandwich" is formed at the immobilised antibody capture zone, leading to development of a coloured line or dot. Conventional lateral flow assays are exemplified by, for example, U.S. Pat. No. 5,656,503 (Unilever Patent Holdings B.V). These assays specify an immobilised antibody capture zone, albeit in a lateral flow format as opposed to the radial format taught by Geigel et al (1982, Clin Chem 28: 1894).

The basic lateral flow format has been modified to enable competition-type assays to be performed. Thus modified lateral flow assays may be based on a labelled mobile component (e.g. coloured particle-labelled antibody), an immobilised component (e.g. an analyte analogue in the form of a stripe or dot) and a membrane through which sample is caused to move by capillary action. In the absence of analyte, the antibody-labelled particle will bind to the immobilised analyte analogue, leading to development of a coloured line or dot, in the presence of analyte, the binding sites on the antibody will be occupied such that the binding of the particle-labelled antibody is reduced or abolished, with a concomitant reduction or abolition of colour. Such an assay is taught, for example, by Biosite (U.S. Pat. No. 5,143,852). Detection of the decrease in colour, however, can be problematical as described above.

Lateral flow assays offer many advantages, including speed, convenience, and relatively low cost. However, they have several drawbacks. The capture component (e.g. antibody) is generally immobilised by adsorption onto the membrane, so variations in membrane and/or antibody batch can lead to variations in the amount of antibody immobilised. Further, some of the antibodies may be only loosely bound and can become mobile when the fluid front passes, leading to loss of signal. Also, since one antibody is immobilised, the only time for it to react with the analyte is as the sample flows past, so sensitivity can be reduced due to the short incubation time. It is also necessary to produce specific coated membranes for each analyte, thus increasing manufacturing costs.

Attempts have been made to address these disadvantages by avoiding the use of an immobilised capture antibody. For example, EP 297292 (Miles), EP 310872 (Hygeia Sciences), and EP 0962771 (Mizuho) describe systems involving a membrane with a trapping zone in conjunction with 2 antibody-coated particles, one unlabelled but large such that it is trapped by the zone, the other small and labelled which can pass through the zone. In the presence of analyte, the small beads become bound to the trapped large beads, leading to formation of a coloured line. Although these methods avoid the use of a pre-immobilised capture antibody, they require two populations of antibody-coated particles in addition to a trapping zone. Frequently such particles are hydrophobic in nature, and thus can be caused to aggregate in a non-specific manner in the presence of biological fluids.

Others have attempted a simpler format, whereby antibody-coated particles capable of free movement through a membrane are caused to agglutinate in the presence of analyte such that their movement is halted. Such agglutination-based immunoassays are known in the art, and rely upon agglutination of particles to which an antigen or antibody is bound to indicate the presence of the corresponding antibody or antigen in a sample. In one of the simpler forms of an agglutination assay, antibodies to a particular analyte are bound to a bead or other visible material.

In particular, U.S. Pat. No. 4,666,863 (Amersham) discloses a method for separating free and bound label by chromatographic means. In one variant, they teach separation of agglutinated and non-agglutinated antibody-coated coloured particles using flow along a membrane. Prior to separation, the reaction mixture is reacted with a cross-linking agent to stabilise the agglutinate. EP 293779 (Daiichi) also discloses a coloured latex agglutination reaction, where agglutinated and non-agglutinated particles are separated by a capillary which allows non-agglutinated latex through but traps the aggregates. EP 280559 (Kodak) describes an assay for multivalent analytes whereby in the absence of analyte label can pass through a filter, but in the presence of analyte an agglutinate is formed which is trapped. U.S. Pat. No. 6,472,226 (Genosis) describes a lateral flow assay without immobilised antibody for very large analytes. They describe a two-zone system, one having large pores and one having small pores, such that analyte can pass through the large pores but becomes trapped on reaching the zone of small pores. This is used in conjunction with a small label (e.g. gold sol to which antibody is attached) which can pass through both zones. In the presence of analyte, a fraction of the antibody-labelled gold sol becomes bound to the analyte and becomes trapped at the small pore zone.

In the main, these agglutination-based assays are restricted to the detection of large analytes with multiple epitopes which enable the formation of large, stable agglutinates. Their effectiveness with smaller analytes having fewer epitopes, or where only a limited number of available epitopes are being used, can be compromised as the reduced number of binding events may result in a weakened aggregate and loss of sensitivity.

An alternative is the so-called membrane agglutination system (Platform Diagnostics, GB patent application 0523124.6), which is based on immunoagglutination within a capillary membrane such that in the presence of analyte, an agglutinate containing a labelled signal moiety is formed which becomes trapped and generates a detectable signal. The technology is an improvement over earlier systems such as that developed by Amersham International plc, but there remain some aspects that could be improved further. First, the "line" formed by the trapped agglutinate is somewhat broad. Whilst in itself not a problem, it differs slightly from that observed in the more common conventional lateral flow assays. This is likely a result of the system having to accommodate the trapping of particle agglutinates of varying sizes, with the smaller ones probably migrating further into the trapping zone. Secondly, any aggregates present in the labelled particle preparation caused by non-analyte mediated interactions may cause a background signal and false-positive results (the same applies to conventional lateral flow assays). Although this can be overcome by suitable conditions for preparing and applying the particles, it would be advantageous to have a system which avoided the need for this, simplifying manufacture and making a more robust system.

In the main, however, prior art membrane agglutination assays are reliant on the sandwich principle to promote an agglutination reaction. Competition or agglutination-inhibition assays (e.g. haemagglutination inhibition assays for the early pregnancy tests) are known in the art, but have mainly been restricted to assays performed on a slide or in a reaction well and where the agglutination is detected visually by observing a change in the pattern of the particles. Since there is no separation of agglutinated and non-agglutinated particles there is no requirement for the formation of strong, stable agglutinates as they are not exposed to strong shear forces, such as capillary forces.

Attempts have been made to perform competition membrane agglutination assays that detect the free or non-agglutinated fraction of particles to avoid the need to detect a reduction in signal at the separation zone. Angenics Inc (U.S. Pat. No. 4,459,361) describe a particle immunoagglutination system whereby agglutinated and non-agglutinated particles are separated by a filter, and one can measure either an increase in the filtrate (non-agglutinated) or decrease in the retentate (agglutinated) fractions. Akers (EP 556202) describes a similar system in which a test mixture is formed by contacting the sample with coloured particles having analyte-specific receptors on their surface. The test mixture is passed through a filter having pores which are larger than the coloured particles but smaller than the particle-analyte aggregates, thus causing trapping of the aggregates. Presence of analyte in the mixture is determined by checking the colour of the filtrate.

An important further problem with the majority of competition assays of the prior art, including many of the competition membrane agglutination systems described, is that the end point is a reduction in signal of the bound label. Whilst this can be accurately assessed using instrumentation to quantify the signal, it is more difficult to achieve with an assay relying on visual detection (e.g. the majority of Point-of-Care assays), especially at low analyte concentrations where the reduction in signal is small. Assays relying on such signal reduction are therefore not popular for such applications. The membrane agglutination systems that measure the non-agglutinated or free fractions suffer from the diffuse signal, and thus a loss of sensitivity, common to measurements of the free fraction in other assay formats.

A competition membrane agglutination format has been devised utilising antibody-labelled signal particles and analyte- or analyte analogue-coated hubs (or vice versa) which overcomes the drawbacks of the prior art. In the absence of sample analyte, the hub molecules cross-link the labelled particles producing a stable agglutinate which becomes trapped in the membrane (and thus a coloured line). In the presence of sample analyte, some of the antibody sites will be occupied and so the agglutination reaction (and thus signal) reduced or abolished.

Immunoassays are known in which an excess of labelled reagent is detected at a so-called 'test complete line', a zone situated at the end of the assay strip comprising immobilised antibody or other binding agent, designed to provide a positive control to confirm the correct flow of solvent and the presence of labelled detection particles. However, such indicators can only be used to reliably report the completion of the test in formats where the labelled reagent is always in excess. They are not, therefore, suitable for saturation assay formats where, in the absence of analyte, most or all of the labelled reagent will be bound in the competition binding step.

STATEMENT OF INVENTION

The invention provides a modified form of saturation assay which addresses many of the issues with the current art. The invention is based on measurement of the free or unbound labelled reagent fraction (such that there is an increase in signal in the presence of analyte), and employs mechanisms to concentrate said unbound, or free, labelled reagent fraction to avoid loss of sensitivity. Such saturation assays may be of any suitable format but are preferably membrane assays.

In particular, the invention provides a modified form of competition assay format comprising the use of a secondary trapping zone, downstream of a primary trapping zone, the secondary trapping zone being capable of trapping unbound, or free, labelled reagent particles. Thus, in the absence of sample analyte, essentially all the labelled reagent particles are trapped at the primary trapping zone and the secondary trapping zone will be clear. However, in the presence of sample analyte some of the labelled reagent particles remain unbound, or free, and so will pass through the primary trapping zone to the secondary trapping zone, where they are then trapped causing the formation of a line.

As will be apparent to a skilled person, this principle of trapping and concentrating the unbound fraction resulting from any saturation assay is applicable to any format of assay in which such a free fraction is separable from the bound fraction, contains detectable signal (preferably visually detectable) and in which the size of such a free fraction is a measure of the original analyte to be measured. The principle is applicable to agglutination assays, where the agglutinated fraction is separated from non-agglutinated particles.

'Saturation assay' as used herein means any assay in which a specific analyte-binding reagent (usually an antibody, but not necessarily) is limiting and there is an excess of analyte and/or analyte-analogue.

'Competition assay' is used in the sense of being one, widely used, version of saturation assay, in which an unlabelled antibody (or some other specific analyte-binding reagent) is used together with a labelled analyte-analogue, which competes with a sample analyte for a limited number of binding sites.

An 'analyte analogue' is a reagent that competes with the analyte for binding sites on the analyte-binding reagent. It may be simply analyte that is immobilised, labelled or chemically modified in some way, and therefore distinguishable, or may be a synthetic or multivalent equivalent of the analyte, depending on the assay format.

In the case of a saturation agglutination assay, it is desirable to form a stable, detectable agglutination reaction within the porous carrier. Although reasonable agglutination can be achieved using large, multi-epitopic analytes where multiple binding events are possible, it can be difficult to achieve stable agglutination with smaller analytes which may contain only a few epitopes. Indeed, for reasons of specificity, it is often desirable to only utilise one or two epitopes on an analyte.

To overcome this, a multivalent carrier molecule, otherwise known as a hub can be used, which comprises multiple binding partners (such as analyte-analogue molecules) firmly bound to a carrier. The resulting hub can then amplifying the binding reaction. In this way it is possible to obtain strong, stable agglutination for small analytes and/or in those situations where only a restricted number of epitopes on the analyte are employed, reducing the need for external stabilizing agents.

A multivalent analyte analogue, therefore, is any moiety presenting a plurality of binding sites for an analyte-binding reagent. One example is a hub molecule to which multiple analyte analogues are attached, conveniently by means of binding partners, such as antibodies. Alternatively, analyte analogues may be attached to hub molecules by other means, such as direct covalent bonding, chemical cross-linking or use of other high affinity binding means such as avidin or streptavidin binding of biotinylated molecules.

The amplification of the binding reaction is achieved by the use of a multivalent hub molecule. The hub may be formed of any suitable material, which is preferably uniform, stable and to which binding partners can be attached. The hub may be soluble or insoluble, although the former is preferred. Examples of hubs include latex beads polystyrene microparticles, glass beads, colloidal gold, cells, for example red blood cells, fibrous materials such as cellulose, and macromolecules such as polysaccharides and proteins. Preferred hubs are polysaccharides, including dextran, preferably aminodextran, agarose, microcrystalline cellulose, starch. Other suitable materials include polyethyleneimine, polyvinyltoluene, or styrenebutadiamine copolymers, polyacrolein microspheres, polyurethane, pollen particles, sporopollenin, polystyrene or polyvinylnapthalene cores surrounded by shells of polyclycidyl methacrylate, microcrystalline cellulose or combinations thereof, polyvinyl alcohol, copolymers of hydroxyethyl methacrylate and methyl methacrylate, silicones and silica, glass, rubber, nylon, diatomaceous earth, silica, etc. Soluble hubs have the advantage of low non-specific binding and increased flexibility, and increased availability of groups for covalent coupling of antibodies or other binding molecules thereto. Preferred soluble hubs are soluble proteins and polysaccharides, including those described above and in particular aminodextran and derivatives thereof. The size of the hub is dictated by factors such as the number of binding partners to be accommodated on the surface, steric factors to ensure stability of the hub throughout the assay, and the nature of the porous carrier in which the assay is to be performed. For example, the hub is preferably small enough to travel through the smallest pores of the membrane in the absence of an agglutination event. Where the hub is formed of insoluble beads, these will be in the region of 0.03-10 µm diameter, preferably 0.05 to 8 µm. For soluble hubs, these may be in the region of 250-2,500 kDa, more preferably 500-2,500 kDa for example for aminodextran molecules.

'Analyte-binding reagent' means any reagent capable of binding the analyte in a specific and reproducible manner and with sufficient affinity to allow the assay to function. In the majority of assays it is convenient for the analyte-binding reagent to be an antibody or effective antigen-binding fragment or derivative of an antibody. Monoclonal antibodies have the advantage of consistent and quantifiable binding properties to defined epitopes. However, for many assay purposes polyclonal IgG fractions are more efficient, having a range of epitope specificities that may be less sensitive to, for instance, conformational changes or steric constraints in the analyte. They also allow, for multi-epitopic analytes, binding to multiple epitopes with the result that analyte molecules may be bound with high avidity. However, depending on the nature of the analyte, other cognate binding molecules may be used, such as receptors (for ligands), ligands or ligand analogues (for receptors), aptamers, ribozymes or polynucleotides.

It will be clear to one of skill in the art that, for some applications and assay formats, it is advantageous to use a multivalent analyte-binding reagent, more preferably in the form of a hub presenting multiple analyte-binding sites, rather than a multivalent analyte-analogue. In many assay formats it is within ordinary skill to devise a variant in which the roles of analyte-analogue and analyte-binding reagent are reversed in terms of which is immobilised, incorporated into a hub, labelled and/or attached to a signal particle, and such variants and adaptations are envisaged by the present invention.

'Labelled reagent' means a particle comprising a detectable moiety and an analyte-binding reagent (or alternatively an analyte or analyte-analogue, depending on the format of the assay). Usually the detectable moiety will be a visually-detectable moiety which allows immobilised concentrations of signal particles to be readily detected by eye. Other forms of detection, such a fluorescence, chemiluminescence, magnetism or radiolabelling are not excluded. The detectable moiety may also provide a means of immobilising the labelled reagent. For example, labelled reagents comprising latex beads may be excluded from a trapping zone of capillary membrane of a pore size too small to allow the latex bead to pass through. The detectable moiety may be either biological or non-biological. Examples of suitable moieties that may be used as components of a labelled reagent include microorganisms, cells, macromolecules, metal sol particles, beads, and charcoal, kaolinite, or bentonite particles. Most preferably, the signal particle comprises coloured latex beads. In a highly preferred embodiment the detectable moiety is agglutinable.

A 'trapping zone' is any means of concentrating and immobilising a fraction, preferably by separation from the remaining fractions of the reaction mixture. Thus, at a trapping zone, a fraction of the reaction mixture such as the unbound fraction, may be separated from the reaction mixture by concentrating and immobilising it at the zone while the remainder of the reaction mixture is allowed to continue past the trapping zone. In this way, said fraction is excluded from downstream flow. Thus, the trapping zone preferably comprises means for separation of one fraction from another.

The competitive binding step results in analyte bound to analyte-binding reagent (often an antibody). In the case of an agglutination assay, the product is an insoluble complex of cross-linked analyte and one or more forms of analyte-binding reagent, in which case this can be conveniently separated from unagglutinated free fraction by physical filtration. In the case of a membrane-bound assay this may be achieved by the flow of fluid passing into a membrane of a smaller pore size, suitable to trap such an insoluble multi-molecular complex, while allowing unagglutinated analyte and labelled analyte-binding reagent to pass through. Such a feature may be termed a primary trapping zone. The primary tapping zone may also trap any aggregates formed by non-analyte mediated means which otherwise could cause a false reaction.

'Secondary trapping zone' means any means of concentrating and immobilising the unagglutinated or unbound fraction resulting from a competitive binding step. A secondary trapping zone may be placed downstream, or distal, to such a primary trapping zone in order to concentrate and immobilise the unbound or free fraction of labelled reagent as hereinbefore described. The secondary trapping zone may also concentrate and immobilise unagglutinated analyte. The labelled reagent may, apart from allowing visual detection, provide a physical means of immobilisation of unagglutinated particles at the secondary trapping zone. These may comprise, for example, particles of colloidal gold or latex beads, which may be trapped by a secondary trapping zone comprising a further membrane of smaller pore size than that used for the primary trapping zone, and which is suitable to trap the size of labelled reagent particles used.

Other formats of assay involve a primary trapping zone that has a direct binding function. In the case of simple capture assays this may comprise immobilised antibodies (or other analyte-binding reagent). Alternatively, 1-site competition assays use immobilised analyte or analyte-analogue to bind labelled antibody. In either case, a functional primary trapping zone immobilises the one product of the competitive binding step, allowing a free fraction to pass through. In the case of such assays, the secondary trapping zone may comprise a further zone of immobilised analyte-binding reagent, analyte, analyte-analogue, or other binding moiety which will immobilise the free signal reagent as appropriate to the format used.

Preferably, a fraction is trapped at the primary and/or secondary trapping zones without binding, for example by restricting its flow through the trapping zone by filtering on the basis of size or other physical parameters such as charge. Preferably, the primary and/or secondary trapping zones are non-immunological, meaning that they do not comprise immunological binding agents to trap the fraction. Trapping zones which do not have a binding function have the advantage that there is no limitation to the amount of fraction trapped, as there would be if binding agents such as antibodies were used to trap the fraction. This has the result of reducing the amount of residual fraction which passes through the trapping zone, and therefore reduces the 'background' signal beyond the trapping zone.

Accordingly, the invention provides a method of performing a saturation binding assay for detecting an analyte in a sample, characterised in that the method comprises a step in which an unbound free fraction of a labelled reagent from a competitive binding event becomes concentrated at a designated trapping zone. Preferably, the labelled reagent comprises a detectable moiety.

Preferably, the saturation binding assay is an immunoassay comprising the steps:
a. competitive binding of the analyte and an unlabelled analyte analogue for a limiting amount of a labelled analyte-binding reagent
b. separation of the fraction of labelled analyte-binding reagent bound to analyte analogue from the free fraction of labelled analyte-binding reagent which is not so bound
c. immobilisation and concentration of the free fraction of analyte-binding reagent
d. detection of immobilised and concentrated free fraction of labelled analyte-binding reagent.

Alternatively, the immunoassay comprises the steps
a. competitive binding of the analyte and a labelled analyte analogue for a limiting amount of an unlabelled analyte-binding reagent
b. separation of the fraction of labelled analyte analogue bound to the analyte-binding reagent from the free fraction of labelled analyte analogue which is not so bound
c. immobilisation and concentration of the free fraction of labelled analyte analogue
d. detection of immobilised and concentrated free fraction of labelled analyte analogue.

In a preferred embodiment, the saturation immunoassay is an agglutination assay comprising the steps
a. competitive binding of the analyte and an unlabelled multivalent analyte analogue to a limiting amount of a labelled analyte-binding reagent
b. separation of agglutinated and non-agglutinated fractions of labelled analyte-binding reagent
c. immobilisation and concentration of the non-agglutinated fraction of labelled analyte-binding reagent
d. detection of immobilised and concentrated labelled analyte-binding reagent.

Alternatively the agglutination assay comprising the steps
a. competitive binding of the analyte and a labelled multivalent analyte analogue to a limiting amount of an unlabelled analyte-binding reagent
b. separation of agglutinated and non-agglutinated fractions of labelled multivalent analyte analogue
c. immobilisation and concentration of the non-agglutinated fraction of labelled multivalent analyte analogue
d. detection of immobilised and concentrated non-agglutinated fractions of labelled multivalent analyte analogue.

Preferably, bound or agglutinated and free or non-agglutinated fractions are separated by means of immobilisation of the bound or agglutinated fraction. More preferably, the bound fraction is immobilised by means of a capillary membrane of a pore size that excludes the bound fraction. Alternatively the bound fraction is immobilised by an immobilised analyte-binding reagent, binding partner or other cognate ligand. In either case, the bound fraction is effectively immobilised at a primary trapping zone.

In an alternative embodiment, the agglutinated and non-agglutinated fractions are separated chromatographically by means of solvent flow through a porous membrane. This embodiment dispenses with a discrete specific primary trapping zone, which immobilises the agglutinated fraction, by using a suitable capillary membrane to separate agglutinated and non-agglutinated fractions on the basis of their particle size. The rate at which particles move with a fluid flow through a capillary membrane is in inverse proportion to their size. Accordingly, the rate at which agglutinates pass through a reaction zone depends upon their size, with large agglutinates moving slowly and smaller agglutinates and single particles moving more rapidly. In a lateral flow format assay, capillary flow proceeds until the solvent front reaches the end of the capillary membrane, when flow of both fluid and particles will cease, with the distance traversed by the particles dependent on the size of the aggregate. Thus, by placing the "secondary" trapping zone (i.e. a region that will trap all particles and agglutinates) at a location along the membrane distal to that reached by the large agglutinates produced in the absence of analyte, a signal will only develop at the trapping zone in the presence of analyte.

This chromatographic format has all the advantages of the other embodiments of the invention with the further improvement that no modified primary trapping zone (i.e. change in membrane pore size, or bound antibody or other reagents) is required and thus manufacturing is simplified and cheaper.

An additional advantage of this format is that it affords improved sensitivity. A physical primary trapping zone may trap both large agglutinates formed in the absence of analyte, and the slightly smaller agglutinates produced in the presence of low levels of analyte. It can be difficult to select a material for the primary trapping zone which can clearly distinguish between the two. However, by using a kinetic, chromatographic format and placing the secondary trapping zone at a suitable location it is possible to discriminate and thus detect lower levels of analyte.

For any of the embodiments described, the unagglutinated or unbound free fraction of labelled reagent may be immobilised and concentrated by means of a secondary trapping zone comprising a capillary membrane of a pore size that excludes or traps the labelled reagent.

Alternatively, the secondary trapping zone may comprise an immobilised analyte-binding reagent or other cognate binding partner or ligand capable of sufficiently high affinity binding to effectively immobilise the free fraction of unagglutinated or unbound labelled reagent and produce a visually detectable indication, such as a coloured line or zone. The nature and colour of the visual signal depends upon the nature of the label attached to the reagent. Colloidal gold, latex particles or other chromogenic labels may be used. Such attached labels, as well as providing the visual signal, may also provide the means of trapping by forming signal particles of convenient dimensions.

In either alternative, the result is a secondary trapping zone that provides a convenient visual indication of the original presence and/or concentration of a selected analyte. The amount of labelled reagent trapped or bound at the secondary trapping zone is, within limits determined by amount of analyte and capacity of the individual assay, proportional to the original analyte concentration being measured.

The method, assay, kit and device of the invention are suitable for detection of any analyte capable of being bound by an analyte-binding reagent. Preferred analytes include proteins, glycoproteins, peptides, or polypeptides, carbohydrates, haptens and nucleic acids. Particularly preferred biologically relevant examples include antibodies, hormones, hormone receptors, antigens, growth factor receptors, vitamins, steroids, metabolites, aptamers, whole organisms (such as fungi, bacteria, viruses, protozoa and multicellular parasites), therapeutic or non-therapeutic drugs, or any combination or fragment thereof. Where the detectable analyte is an antibody, the analyte binding reagent may be an antigen, antigen-analogue, hapten, hapten-analogue or a second antibody with specificity for the antibody to be measured.

Preferably, the analyte may be an immunologically active protein or polypeptide, such as an antigenic polypeptide or protein. Most preferred analytes for detection by the present invention include hCG, LH, FSH, and antibodies to HIV.

It is envisaged that the present invention may be used for the detection of two or more analytes in a single assay, preferably even a single sample. Thus, in any assay, two or more secondary trapping zones may be provided, each being specific for trapping a particular labelled reagent. The labelled reagents may be distinguishable by any suitable means, for example, colour.

In a further aspect, the invention provides a kit for performing a saturation assay for detection of an analyte in a sample, the kit comprising:
a. means for separating bound and unbound fractions of a competitive binding step
b. a secondary trapping zone Preferably the kit further comprises a porous carrier.

More preferably, the means for separating bound and unbound fractions of a competitive binding step comprises a primary trapping zone.

In one preferred embodiment the saturation assay is an agglutination immunoassay and the primary trapping zone comprises a means for immobilising an agglutinated fraction. Preferably the primary trapping zone comprises a capillary membrane of a pore size that excludes the bound or agglutinated fraction.

Alternatively, the means for separating bound and unbound fractions of a competitive binding step comprises a capillary membrane of a pore size that allows chromatographic separation of bound and unbound products on the basis of particle size. In a highly preferred embodiment the competitive binding step is an agglutination step and the chromatographic separation separates agglutinated complexes from unagglutinated components.

Preferably, the kit comprises a labelled reagent, as hereinbefore described.

It is preferred that the secondary trapping zone comprises means to immobilise and concentrate a free fraction of labelled binding reagent. In one embodiment the secondary trapping zone comprises a capillary membrane of a pore size that excludes free or unagglutinated labelled reagent. Alternatively, the secondary trapping zone may comprise an immobilised analyte-binding reagent or other cognate binding partner or ligand capable of sufficiently high affinity binding to effectively immobilise the free or unagglutinated fraction and produce a visually detectable indication, such a coloured line or zone.

Preferably the kit further comprises a. a multivalent analyte analogue, preferably comprising a hub, to which two or more analyte-analogue moieties are bound, and b. two or more labelled analyte-binding reagents capable of binding said analyte-analogue moieties Alternatively, the kit further comprises a. a hub to which two or more analyte-binding reagents are bound, and b. two or more labelled analyte-analogue moieties capable of binding said analyte-binding reagents.

Preferably the kit further comprises one or more further components selected from the list consisting of buffers, application means (such as pipettes), instructions, charts, desiccants, control samples, dyes, batteries and/or signal processing/display means.

It is also preferred that the porous carrier is a solid matrix, preferably fibrous.

More preferably, the pore size upstream of the primary trapping zone is sufficient to allow free movement of the hub, labelled reagent, sample and any bound fraction or agglutinate.

In a final aspect, the invention also provides a device for performing a saturation assay for detection of an analyte within a sample, the device comprising a carrier having a proximal end for receiving a sample, and a distal end toward which a sample may travel along the carrier, wherein the carrier comprises:

a. a primary trapping zone comprising means which exclude a bound fraction, and b. a secondary trapping zone comprising mans which exclude a labelled reagent.

Preferably, the carrier is porous. Preferably, the primary and/or secondary trapping zones comprise a capillary membrane of a pore size which excludes a bound fraction or labelled reagent, respectively.

Preferably the device further comprises, in a dried, reconstitutable form, a hub to which two or more analyte-binding reagents or, alternatively, analyte-analogue moieties, are bound. The device is preferably housed in a casing, or receptacle, which more preferably will be hand-held.

BRIEF DESCRIPTION OF THE FIGURES

The present invention will be described below by way of non-limiting examples, and with reference to the drawings, in which:

FIG. 1. shows the assembly of test strips with a primary agglutinate trapping membrane.

FIG. 2. shows the assembly of test strips with a chromatographic agglutinate separation membrane.

FIG. 3. shows a photograph of positive vs negative example test results.

DETAILED DESCRIPTION

Example 1

Preparation of Antibody-Coated Polystyrene Microparticles

1. Combine 100 µl 200nm blue polystyrene microparticles 10% solids ('latex') (Polymer Labs, Shropshire, UK), 200 µl absolute ethanol, 43 µl sheep FITC antiserum (Micropharm, Carmarthenshire, UK) and 657 µl 10 mM phosphate buffer pH 7.4.
2. Incubate at room temperature for 2 hours, with gentle agitation, to allow antibody adsorption to occur.
3. Add 200 µl 6% BSA in 10 mM phosphate buffer pH 7.4 and continue incubation with agitation for 1 hour.
4. Centrifuge adsorption mixtures for 20 minutes at 4000 g, followed by 5 minutes at 8000 g, to form a soft latex pellet.
5. Remove supernatant and replace with 1 ml latex dilution buffer (Omega Diagnostics, Alva, UK). Gently resuspend pellet.
6. Collect latex pellet by centrifugation and wash as described in 5.
7. Repeat step 6 twice further and finally resuspend latex pellet in 900 µl latex dilution buffer.
8. Adjust latex solids to 1% w/v, by comparison with a standard dilution series, assessed by light absorbance at 690 nm.
9. Confirm antibody adsorption by slide agglutination assays, mixing 2 µl 1% solids anti-FITC latex with 1 µl FITC-dextran 10-300 ng/µl in 10 mM phosphate buffered saline pH7.4 (Sigma-Aldrich, FD2000S).

Example 2

Preparation of Antibody-Coated Polystyrene Microparticles

1. Combine 100 µl 200 nm blue polystyrene microparticles 10% solids ('latex') (Polymer Labs, Shropshire, UK), 200 µl absolute ethanol, 750 µg mouse IgG (Sigma, 15381) in 10 mM phosphate-buffered saline pH 7.4, 110 µg anti-hCG (Medix Biochemica, Kauniainen, Finland, clone #5006) in 10 mM phosphate-buffered saline pH 7.4. Adjust volume to 1 ml with 10 mM phosphate buffer pH 7.4.
2. Incubate at room temperature for 2 hours, with gentle agitation, to allow antibody adsorption to occur.
3. Add 200 µl 6% BSA in 10 mM phosphate buffer pH 7.4 and continue incubation with agitation for 1 hour.
4. Centrifuge adsorption mixtures for 10 minutes at 3500 g to form a soft latex pellet.
5. Remove supernatant and replace with 1 ml latex dilution buffer (Omega Diagnostics, Alva, UK). Gently resuspend pellet.
6. Collect latex pellet by centrifugation for 20 minutes at 8000 g and wash pellet as described in 5.
7. Repeat step 6 twice further and finally resuspend latex pellet in 500 µl latex dilution buffer.
8. Adjust latex solids to 1% w/v, by comparison with a standard dilution series, assessed by light absorbance at 690 nm.
9. Confirm antibody adsorption by slide agglutination assays, mixing 2.5 µl 1% solids of the 'test' latex prepared here, with an equal quantity of 'control' latex coated with an appropriate antibody 'sandwich partner' (prepared and validated previously using the same method), plus 5 µl hCG solution 0-250 IU/ml in 'synthetic urine' i.e. (approx. 4.5 g/l KCl, 7.5 g/l NaCl, 4.8 g/l sodium phosphate (monobasic), 18.2 g/l urea, 2 g/l creatinine, 50 mg/l HSA) (hCG concentration value assigned against $4^{th}$ I.S., NIBSC).

Example 3

Preparation of hCG Hub Reagent

1. Desalt the anti-hCG (alpha-subunit) into 0.1 M phosphate pH 7.5 buffer, using a 1.6×15 cm G25M Sephadex column, and determine concentration and yield.
2. Activate the anti-hCG antibody, using 8 molar equivalents of NHS-PEG-MAL. Incubate the reaction mixture at 20° C. for two hours. Quench the reaction with 100 molar equivalents of glycine and desalt the maleimide-activated anti-hCG into 5 mM EDTA, PBS pH 7.3 buffer using two shots down a 1.6×15 cm G50F Sephadex column. Determine concentration and yield of activated antibody.
3. Activate a 500 kDa aminodextran using 1000 molar equivalents of 2-Iminothiolane (2-IT). Incubate the reaction mixture at 20° C. for 110 minutes. Desalt the thiol activated aminodextran into 5 mM EDTA, PBS pH 7.3 buffer, using G25M Sephadex media. Determine incorporation ratio of thiol:aminodextran using the Ellman's assay.
4. Add 25 Molar equivalents of the maleimide-activated anti-hCG antibody to the thiol-activated aminodextran and incubate the reaction mixture at 15° C. for 16 hours. Quench the reaction mixture with 1000 equivalents of N-ethylmaleimide. Purify the conjugate on a 2.6×50 cm Superdex 200PG column using 50 mM PBS pH 7.2 buffer as eluant. Determine the concentration and yield of conjugate, then filter through a 0.2 µm Minisart filter.
5. Finally, 'pre-saturate' the anti-hCG aminodextran conjugate with hCG, by combining 70 µl anti-hCG aminodextran conjugate (21.6 ng/µl) with 30 µl hCG solution (178.5 IU/ml in 'synthetic urine' i.e. (approx. 4.5 g/l KCl, 7.5 g/l NaCl, 4.8 g/l sodium phosphate (monobasic), 18.2 g/l urea, 2 g/l creatinine, 50 mg/l HSA) and incubate for 30 minutes at 4° C.

Example 4

Preparation of Test Strips with a Primary Agglutinate Trapping Membrane

Membrane materials were cut to size as follows:
1. Wick, e.g. Conjugate release pad 8964 (Ahlstrom), 20 mm×50 mm.
2. Primary agglutinate trapping membrane, e.g. Fusion 5 (Whatman), 4 mm×50 mm.
3. Intermediate membrane, e.g. Conjugate release pad 8964 (Ahlstrom), 10 mm×50 mm.
4. Free fraction concentration membrane, e.g. Z-bind PES membrane 0.2 µm (PALL), 3 mm×50 mm.
5. Absorbent sink, e.g. Absorbent Pad 222 (Ahlstrom), 50 mm×50 mm.
6. Self-adhesive plastic (×2), e.g. 0.04" Clear polyester with D/C hydrophilic PSA (G&L) 70 mm×100 mm.

A composite 'card' of the above materials was assembled as shown in FIG. 1. Adjacent membrane materials were aligned, as shown, to ensure good fluid transfer between successive sections of the strip. The second sheet of self-adhesive plastic was applied firmly to the upper surface, leaving approximately 10 mm of the wick exposed, to allow application of sample/reagents. The resulting 'card' was sliced into 4 mm strips and any excess plastic trimmed.

Example 5

Preparation of Test Strips with a Chromatographic Agglutinate Separation Membrane Membrane materials were cut to size as follows:
1. Wick/separation membrane, e.g. Conjugate release pad 8964 (Ahlstrom), 100 mm×50 mm.
2. Free fraction concentration membrane, e.g. Z-bind PES membrane 0.2 µm (PALL), 4 mm×50 mm.
3. Absorbent sink, e.g. Absorbent Pad 222 (Ahlstrom), 10 mm×50 mm.
4. Self-adhesive plastic (×2), e.g. 0.04" Clear polyester with D/C hydrophilic PSA (G&L) 70 mm×120 mm.

A composite 'card' of the above materials was assembled as shown in FIG. 2. Adjacent membrane materials were aligned, as shown, to ensure good fluid transfer between successive sections of the strip. The second sheet of self-adhesive plastic was applied firmly to the upper surface, leaving approximately 10 mm of the wick exposed, to allow application of sample/reagents. The resulting 'card' was sliced into 4 mm strips and any excess plastic trimmed.

Example 6

Test for Fluorescein using Test Strips with a Primary Agglutinate Trapping Membrane 1. Anti-FITC latex 2 µl of 1% w/v solids (prepared in house as described in Example 1) was mixed with 1 µl of fluorescein solution and incubated at room temperature for 10 minutes.
2. FITC-dextran 'hub', 1 µl of 30 ng/µl in phosphate buffered saline pH7.4, was added to the above mixture and incubated for a further 5 minutes.
3. The above reaction mixture was then applied to the proximal 'wick' end of a test strips with a primary agglutinate trapping membrane (assembled as described in example 4), followed by approximately 300 µl latex dilution buffer (Omega Diagnostics, Alva, UK), which was applied in 3 shots of 100 µl.

The following results, read at the free fraction concentration membrane, were obtained:

TABLE 1

|  | Fluorescein conc. ng/µl | Signal |
|---|---|---|
| Experiment 1 | 0 | − |
|  | 0.1 | +/− |
|  | 0.3 | + |
|  | 1 | + |
|  | 3 | + |
|  | 10 | + |
|  | 30 | + |
|  | 100 | + |
| Experiment 2 | 0 | +/− |
|  | 1 | ++ |
|  | 3 | ++ |
|  | 10 | ++ |
|  | 30 | ++ |
|  | 100 | ++ |
|  | 300 | ++ |

Example 7

Test for Fluorescein using Test Strips with a Chromatographic Agglutinate Separation Membrane Tests were performed as described in example 6, using test strips with a chromatographic agglutinate separation membrane (prepared as described in example 5).

The following results, read at the free fraction concentration membrane, were obtained:

TABLE 2

|  | Fluorescein conc. ng/µl | Signal |
| --- | --- | --- |
| Experiment 1 | 0 | − |
|  | 0.03 | +/− |
|  | 0.1 | +/− |
|  | 0.3 | ++ |
|  | 1 | ++ |
|  | 3 | ++ |
|  | 10 | ++ |
| Experiment 2 | 0 | − |
|  | 0.03 | +/− |
|  | 0.1 | +/− |
|  | 0.3 | + |
|  | 1 | + |
|  | 3 | ++ |
|  | 10 | ++ |

Example 8

Test for Anti-FITC using Test Strips with a Primary Agglutinate Trapping Membrane 1. Sheep FITC antiserum was diluted (as indicated below) in normal sheep serum (Micropharm, Carmarthenshire, UK).
2. 1 µl of each diluted antiserum was mixed with 1 µl FITC-dextran 'hub' (10 ng/µl in phosphate buffered saline pH7.4) and incubated at room temperature for 10 minutes.
3. 2 µl of anti-FITC latex 1% w/v solids (prepared in house as described in example 1) was added to the above mixture and incubated for a further 5 minutes.
4. The above reaction mixture was then applied to the proximal 'wick' end of a test strip with a primary agglutinate trapping membrane (assembled as described in example 4), followed by approximately 300 µl phosphate buffered saline pH7.4, which was applied in 3 shots of 100 µl.

The following results, read at the free fraction concentration membrane, were obtained:

TABLE 3

| FITC antiserum dilution | Signal |
| --- | --- |
| 0 | +/− |
| 1:10 | + |
| 1:3 | + |
| 1:1 | + |

Example 9

Test for Anti-FITC using Test Strips with a Primary Agglutinate Trapping Membrane 1. Sheep FITC antiserum was diluted (as indicated below) in normal sheep serum (Micropharm, Carmarthenshire, UK).
2. 1 µl FITC-dextran 'hub' (30 ng/µl in phosphate buffered saline pH7.4) was mixed with 1 µl of a 1:100 FITC antiserum and pre-incubated at room temperature for 10 minutes.
3. 1 µl of each diluted antiserum was added to 2 µl pre-incubated FITC-dextran 'hub' (above) and incubated at room temperature for 10 minutes.
4. 2 µl of anti-FITC latex 1% w/v solids (prepared in house as described in example 1) was added to the above mixture and incubated for a further 5 minutes.
5. The above reaction mixture was then applied to the proximal 'wick' end of a test strip with a primary agglutinate trapping membrane (assembled as described in example 4), followed by approximately 300 µl phosphate buffered saline pH7.4, which was applied in 3 shots of 100 µl.

The following results, read at the free fraction concentration membrane, were obtained:

TABLE 4

| FITC antiserum dilution | Signal |
| --- | --- |
| 0 | − |
| 1:3000 | − |
| 1:1000 | +/− |
| 1:300 | +/− |
| 1:100 | ++ |
| 1:30 | + |
| 1:10 | + |
| 1:3 | + |

Example 10

Test for hCG using Test Strips with a Primary Agglutinate Trapping Membrane

1. Anti-hCG latex (2 µl) (prepared as described in example 2) was mixed with 2 µl of synthetic urine (see example 3) containing hCG ('sample') and incubated for 10 minutes at room temperature.
2. Pre-saturated hCG hub reagent (4 µl) (prepared as described in example 3) was combined with the above mixture and allowed to react for 2-5 minutes.
3. The above reaction mixture was then applied to the proximal 'wick' end of a test strip with a primary agglutinate trapping membrane (assembled as described in example 4, with the exception that the primary agglutinate trapping membrane size was reduced to 3 mm×50 mm), followed by approximately 300 µl latex dilution buffer (see above), which was applied in 3 shots of 100 µl.

The following results, read at the free fraction concentration membrane, were obtained:

TABLE 5

| HCG concentration (IU/ml) | Signal |
| --- | --- |
| 0 | +/− |
| 0.25 | +/− |
| 0.5 | +/− |
| 6.25 | ++ |
| 62.5 | +++ |

The invention claimed is:

1. A method of performing a saturation assay for detecting an analyte in a sample, comprising:
   a. providing a labeled analyte analogue and an unlabeled analyte binding reagent;
   b. concentrating a bound fraction of labeled analyte analogue resulting from a competitive binding event between the analyte and the labeled analyte analogue for the unlabeled analyte binding reagent at a primary trapping zone;

c. concentrating a free or unbound fraction of labeled analyte analogue which is not bound to the unlabeled analyte binding reagent at a secondary trapping zone; and d. detecting the free or unbound fraction of the labeled analyte analogue concentrated at the secondary trapping zone, wherein the primary trapping zone comprises a capillary membrane of a pore size which concentrates the bound fraction of labeled analyte analogue, and the secondary trapping zone comprises a capillary membrane of a pore size which concentrates the free or unbound fraction of labeled analyte analogue, and wherein the amount of the free or unbound fraction of the labeled analyte analogue concentrated at the secondary trapping zone is indicative of the amount of analyte in the sample.

2. The method of claim 1, wherein the saturation assay is an agglutination assay, the labeled analyte analogue is a labeled multivalent analyte analogue, the bound fraction of labeled analyte analogue is an agglutinated fraction of the labeled multivalent analyte analogue, and the free or unbound fraction of labeled analyte analogue is a non-agglutinated fraction of the labeled multivalent analyte analogue.

3. The method according to claim 1, wherein concentration of the bound fraction and/or free or unbound fraction results in immobilization of said fraction(s).

4. The method according to claim 1 wherein the free or unbound fraction of labeled analyte analogue concentrated at the secondary trapping zone provides a visually detectable indication.

5. A method of performing a saturation assay for detecting an analyte in a sample, comprising:

a. providing an unlabeled analyte analogue and a labeled analyte-binding reagent;

b. concentrating a bound fraction of labeled analyte-binding reagent resulting from a competitive binding event between the analyte and the analyte analogue for the labelled analyte-binding reagent at a primary trapping zone;

c. concentrating a free or unbound fraction of labeled analyte-binding reagent which is not bound to analyte analogue at a secondary trapping zone; and d. detecting the free or unbound fraction of the labeled analyte-binding reagent concentrated at the secondary trapping zone, wherein the primary trapping zone comprises a capillary membrane of a pore size which concentrates the bound fraction of labeled analyte-binding reagent, and the secondary trapping zone comprises a capillary membrane of a pore size which concentrates the free or unbound fraction of labeled analyte-binding reagent, and wherein the amount of the free or unbound fraction of the labeled analyte-binding reagent concentrated at the secondary trapping zone is indicative of the amount of analyte in the sample.

6. The method of claim 5, wherein the saturation assay is an agglutination assay, the unlabeled analyte analogue is a multivalent analyte analogue, the bound fraction of labeled analyte-binding reagent is an agglutinated fraction of the labelled analyte-binding reagent, and the free or unbound fraction of labeled analyte-binding reagent is a non-agglutinated fraction of the labeled analyte-binding reagent.

7. The method according to claim 6 wherein the agglutinated and non-agglutinated fractions of the labeled analyte-binding reagent are separated chromatographically by solvent flow through a porous membrane.

8. The method according to claim 5, wherein concentration of the bound fraction and/or free or unbound fraction results in immobilization of said fraction(s).

9. The method according to claim 5, wherein the free or unbound fraction of labeled analyte-binding reagent concentrated at the secondary trapping zone provides a visually detectable indication.

\* \* \* \* \*